United States Patent
Rodrigues De Faria

(10) Patent No.: US 10,407,661 B2
(45) Date of Patent: Sep. 10, 2019

(54) METHOD FOR PACKAGING FUNGAL SPORES IN A MODIFIED ATMOSPHERE WITH A VIEW TO INCREASING THE SHELF LIFE OF THE FUNGI

(75) Inventor: Marcos Rodrigues De Faria, Brasilia-DF (BR)

(73) Assignee: EMPRESA BRASILEIRA DE PESQUISA AGROPECUÁRIA—EMBRAPA, Brasília (BR)

( * ) Notice: Subject to any disclaimer, the term of this patent is extended or adjusted under 35 U.S.C. 154(b) by 8 days.

(21) Appl. No.: 13/813,326

(22) PCT Filed: Aug. 1, 2011

(86) PCT No.: PCT/BR2011/000254
§ 371 (c)(1),
(2), (4) Date: Apr. 26, 2013

(87) PCT Pub. No.: WO2012/012858
PCT Pub. Date: Feb. 2, 2012

(65) Prior Publication Data
US 2013/0203154 A1    Aug. 8, 2013

(30) Foreign Application Priority Data
Jul. 30, 2010 (BR) .................................. 1002615

(51) Int. Cl.
| | |
|---|---|
| *C12N 1/14* | (2006.01) |
| *C12M 1/00* | (2006.01) |
| *C12N 1/04* | (2006.01) |
| *B65B 55/00* | (2006.01) |

(52) U.S. Cl.
CPC ................ *C12N 1/14* (2013.01); *B65B 55/00* (2013.01); *C12M 45/22* (2013.01); *C12N 1/04* (2013.01)

(58) Field of Classification Search
CPC .......... A61K 8/0204; C12N 1/14; C12N 1/04; C12R 1/645; C12M 45/22
See application file for complete search history.

(56) References Cited

U.S. PATENT DOCUMENTS

2009/0071855 A1 * 3/2009 Bahuguna et al. ........... 206/438

OTHER PUBLICATIONS

Faria, "Studies on Entomopathogenic Fungi: Evaluations of Germination Protocols for Assessing Conidial Quality and Modified Atmosphere Packaging for Enhancing High Temperature Shelf Life", a dissertation of Cornell University, Aug. 2009.*

* cited by examiner

*Primary Examiner* — Ruth A Davis
(74) *Attorney, Agent, or Firm* — Sughrue Mion, PLLC

(57) ABSTRACT

The present invention relates to a packaging method for increasing the shelf life of fungal spores and to the packaging that contains such spores. The packaging method comprises the steps of pre-drying the spores to a water activity range viable for the fungus of interest, followed by packing of the spores into gas- and water-vapor-impermeable packaging by means of the use of sachets, thereby providing an atmosphere of low relative humidity and low oxygen content, followed by keeping of the spores in the packaging for a certain period of time at the temperature suitable for the spores prior to the exposure thereof to high temperatures.

9 Claims, 2 Drawing Sheets

METHOD FOR PACKAGING FUNGAL SPORES IN A MODIFIED ATMOSPHERE WITH A VIEW TO INCREASING THE SHELF LIFE OF THE FUNGI

FIELD OF THE INVENTION

The present invention relates to methods for packaging fungal spores, such as entomopathogenic fungi of the genera *Beauveria, Isaria, Lecanicillium, Nomuraea, Metarhizium* and *Trichoderma*, to increase the shelf-life.

BACKGROUND OF THE INVENTION

Biological pesticides are an alternative to those obtained synthetically, because they are not toxic to humans. Among them are those produced from entomopathogenic fungi, whose spores are dehydrated in order to remain viable for extended periods (Moore et al. Effects of moisture content and temperature on storage of *Metarhizium flavoride* conidia. Biocontrol Science and Technology, v. 6, p. 51-61). Dehydration also allows spores to survive in extreme environments characterized by dry heat, freezing and thawing, as well as acidic medium.

For more than a century research has shown the interaction between fungi and agricultural pests. Such interaction promotes the development of crop plants through the elimination of their pathogens, insect pests and weeds. Such findings have stimulated the use of mycopesticides to control agricultural pests. The production of biopesticides has increased and, among the causes of this increase are the demand of consumers for healthier foods, foods with less toxic waste, greater awareness of industry professionals regarding the use of agricultural pesticides, increasingly restrictive legislation on chemical pesticides and the need to use alternative products in programs to manage the resistance to chemical.

Fungi used in the biological control of pests and are used as pesticides are exposed to high temperatures, reaching 50° C. or more during transport or storage. This environmental factor affects the viability of fungal spores sensitive to temperature rises, such as *Metarhizium, Beauveria, Lecanicillium* and *Trichoderma*. The studies carried out to date were directed especially to storage of said fungi under refrigerated conditions or ambient temperatures below approximately 30° C. Mycopesticides experience rapid decline in viability during storage without refrigeration and it compromises product acceptance in the market, causing undesirable results in control of target pests.

The study by Marques and Alves (Marques, E J., Alves, S. R. "Otimizagao de formulações na preservagao de esporos de *Beauveria bassiana* (Bals.) Vuill. e *Metarhizium anisopliae* (Metschn.) Sorok em diferentes condições de armazenamento. [Optimization of formulations in the preservation of spores of *Beauveria bassiana* (Bals.) Vuill. and *Metarhizium anisopliae* (Metschn.) Sorok at different storage conditions] Arquivos de Biologia e Tecnologia, v. 39, p. 861-877, 1996) demonstrated that the viability of spores having moisture content of 15.5% stored at 30° C. can be greatly reduced in less than 30 days.

The study of Sandhu et al. (Sandhu, S. S., Rajak, R. C., Agarwal, G. P. Studies on prolonged storage of *Beauveria bassiana* conidia: effects of temperature and relative humidity on conidial viability and virulence against chikpea borer. *Helicoverpa armigera*. Biocontrol Science and Technology, v. 3, p. 47-53, 1993) disclosed that the lower the relative temperature and humidity of the equilibrium adopted during storage, the longer the viability of *Beauveria bassiaria* spores is preserved.

Great emphasis has been given to the storage of entomopathogenic fungi and other species in environments with low or moderate temperature or in packages which allow exchange between the atmospheres inside and outside, which do not constitute suitable methods for storage at temperatures above 25° C.

Document U.S. Pat. No. 5,989,898 discloses the use of impermeable packages and humidity and oxygen absorbers to generate atmosphere with relative humidity of less than 10% and less than 5% oxygen. The document also proposes the elimination of oxygen by vacuum packaging, or by applying nitrogen to the package with spores.

The microorganisms used were *Beauveria bassiana* and *Metarhizium anisopliae* for storage at 25° C. and 37° C. Document U.S. Pat. No. 5,989,898 uses a surfactant agent to reactivate the spores, differing from the present invention, which allows storage at temperatures above 37° C., using different nontoxic gases ($CO_2$, $H_2$ and He) in substitution to oxygen, and adopts the observance of a pre-incubation period of the packaged product. It is important that properly packaged mycopesticides be exposed to suitable temperature conditions before being exposed to extreme conditions to allow the levels of oxygen and moisture to reduce to suitable levels. WO 9,718,294 discloses a two- to six-fold extension of the shelf-life of fungal spores or bacteria by reducing the oxygen content, associated or not with moisture reduction methods. However, the maximum storage temperature evaluated was 30° C., and after only 70 days of storage the initial viability was reduced by 85% or more in the treatment employing an $O_2$ absorber sachet or in the treatment employing nitrogen. The present invention allows for maintenance of viability of fungal spores stored at higher temperatures, e.g. 40° C. over a period of three to six months.

SUMMARY OF THE INVENTION

It is an object of the present invention to provide a method for packing fungal spores with a view to increasing their shelf life. The method comprises the steps of: i) reducing the initial humidity content of the spores to a water activity range viable to the organisms; ii) placing the spores into gas- and water-vapour-impermeable packaging with at least one moisture and oxygen absorbing agent; iii) keeping of the spores in the packaging for a minimum of two days at between 15 and 25° C., preferably at 25° C. or other temperature suitable for the organisms prior to the exposure thereof to high temperatures.

A second embodiment of the invention consists in providing spores of the genera *Beauveria, Isaria, Lecanicillium, Nomuraea, Metarhizium* and *Trichoderma*, with increased shelf-life.

In another embodiment a sealed package is obtained comprising in the inside: (i) viable spores of fungi; and (ii) an environment with reduced moisture content and oxygen by the use of sachets and with an incubation period at a suitable temperature in gas- and water-vapour-impermeable packaging.

DETAILED DESCRIPTION OF THE INVENTION

Figure 1:
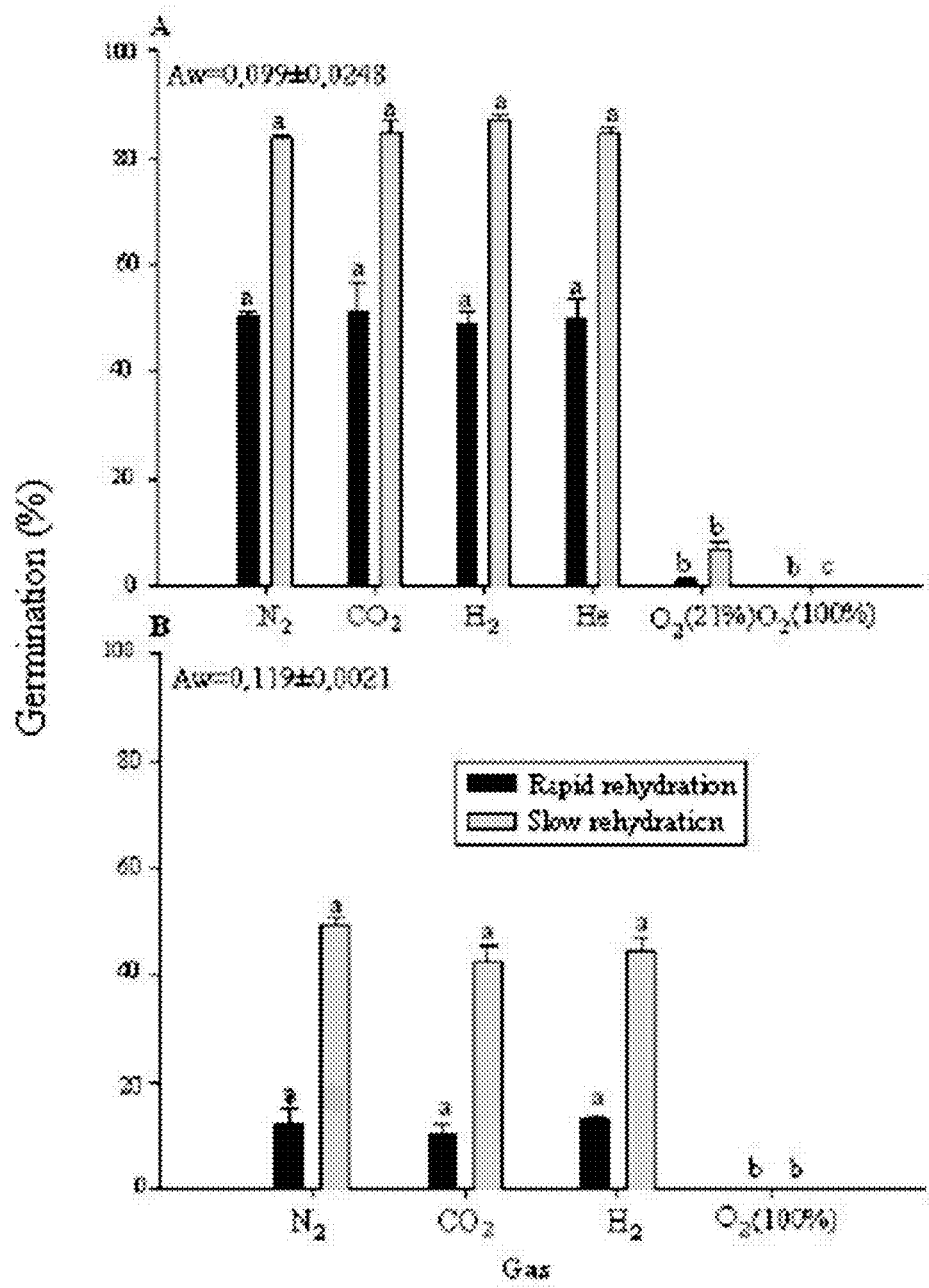
FIG. 1: Effect of different gases in *Beauveria bassiana* conidial viability after storage at 50° C. for 60 days. Viability was assessed by means of two protocols for germination (rapid rehydration vs. Slow rehydration).

The present invention relates to a storage method for increasing the shelf-life of fungi under non-refrigerated conditions, particularly temperatures higher than or equal to 37° C. By means of this methodology the spores remain viable even when subjected to high ambient temperatures.

In the description that follows, certain terms are extensively used. Then following definitions are provided to facilitate understanding of the invention.

The term "modified atmosphere packaging" is herein defined as the process where the packaging material inside said package is exposed to gas having a different composition from atmospheric air, and may include techniques such as injection of a certain gas or mixture of gases inside the packing or the use of elements whose components react with components of the packaging. These elements may be but are not limited to absorbing sachets, gas emitters or water vapour absorbers.

The term "viability" refers to the percentage of germination of spores measured by a procedure which employs rapid rehydration, for being considered a more suitable protocol for assessment of the conidial quality of mycopesticides.

It is considered "viable temperature to the organism" one that does not cause death or debilitation of conidia of certain species. In the present invention the viable temperature is preferably close to 25° C.

"Water activity" ($a_w$) is defined as the ratio of the pressure of water vapour of a material and the pressure of the vapour of pure water at the same temperature. It is a measurement of the water contained in the material which is available for chemical and biological reactions and, therefore, it is an important parameter in studies with microorganisms.

For the purposes of the present invention, "pre-incubation period" or "equilibration period" is the time the spores are kept in the impermeable packaging prior to exposure to high temperatures, this time is needed to reduce water activity to values lower than 0.1, preferably between 0.02 and 0.03.

The term "shelf-life" is defined as the time period in which a mycopesticide may be stored in a specific temperature condition without considerable loss of the attributes related to its efficacy. For mycopesticides packaged in non-hermetic packages, storage relative humidity should be also considered. For the purposes of the present invention, it is considered the period of 2 to 6 months the minimum desirable shelf life for biological insecticides stored at temperatures close to 40° C. Viability is the attribute most commonly used by pathologists to refer to the conidial quality and should preferably be greater than 80%. Therefore, it was established as shelf-life for mycoinsecticides the time required for the viability to be reduced to 80% at a determined temperature.

The method of extending the shelf-life of spores of entomopathogenic fungi consists of the following steps:

i) reducing the initial humidity content of the spores to very low levels of water activity viable for the organisms;

ii) placing the spores into gas- and water-vapour impermeable packaging with one oxygen absorber agent and one humidity absorber agent, and these agents are preferably in the form of sachets. Optionally, a single sachet capable of absorbing both oxygen and humidity can be used.

iii) keeping the spores in the packaging for at least days at a mild temperature prior to exposure to high temperatures.

Reduction of the initial humidity content of hydrated spores can be achieved by drying during the step of harvesting the spores. The production of fungi normally occurs in solid substrates, such as boiled rice and the like. Immediately after the process of producing fungi the colonized substrate can be conditioned in a room with low relative humidity, resulting in drying of conidia or using a chamber containing desiccant material until reduction of water activity to low values occurs.

Such low values of water activity prior to filling are preferably lower than 0.1. This material may be selected from the group of, but not being limited to: calcium sulfate and silica gel. For the reduction in humidity content in the drying chamber to occur it is necessary to wait for a period of two days or longer at lower temperatures, preferably between 15 and 25° C., more preferably at about 25° C. or other temperature that does not affect spore viability, in which the dehydration of the fungus can occur without weakening the fungal structure.

The water activity of the organisms is significantly reduced after filling, and thus maintained through the use of gas- and water-vapour-impermeable packaging.

In the packaging process of spores, as a means to provide proper atmosphere for the conservation thereof, preferably, sachets containing humidity and oxygen absorber agents are used. These sachets can have only one function, that is, they are individually oxygen absorbers or humidity absorbers, or can have dual function when a single sachet acts as oxygen and humidity absorber. The sachets should generate non-toxic atmosphere to spores. As humidity absorbers, calcium sulfate or silica gel can be used. Useful Sachets for the present invention may be selected from but are not limited to: RP-3A (oxygen and humidity absorber), Ageless® ZPT 1000 (oxygen absorber), OxyFree™ 504A (oxygen and carbon dioxide absorber), OxyFree™ 504E (oxygen absorber and carbon dioxide generator) or anhydrous calcium sulfate (humidity aborber). The impermeable packages used in the method of the present invention can be, but are not limited to aluminized packages and glass.

The result of using sachets for packaging is different, depending on the initial water activity of the spores. When using only oxygen absorber sachet, the high humidity of the spores affects the preservation of the same, reducing viability after exposure to high temperature conditions. Humidity absorbers that do not release water vapour when exposed to high temperatures should be used, such as Drierite™, anhydrous calcium sulfate compound, which only releases water vapour after exposure to temperatures above 177° C.

The water activity of the final mycopesticide and the atmospheric composition inside the package are essential factors for maintaining the viability of the spores until use. The time spores are kept in the impermeable packaging prior to exposure to high temperatures is referred to as pre-incubation or "equilibration period", this time is needed to reduce water activity to values lower than 0.1, preferably between 0.02 and 0.03. For the fungus *Beauveria bassiana*, for example, the equilibration period is usually two days for small amounts of spores or more, depending on factors such as the size of the package, type of formulation, the amount of mycopesticide and the amount and efficiency of the absorber sachets used.

The fungi that can be packaged and reactivated in accordance with the present invention include, but are not limited to, those of the genera *Beauveria, Isaria, Lecanicillium, Nomuraea, Metarhizium* and *Trichoderma*.

The impermeable packaging wherein fungal spores according to the invention are packaged can be, but are not limited to: glass, laminate materials containing aluminum or ceramic or other gas- and water-vapour-impermeable materials.

The following examples have the purpose of illustrating and further elucidating the invention and shall not be considered as a form of limiting the invention.

EXAMPLES

Example 1

Injection of Different Gases in Glass Packaging

Samples of *Beauveria bassiana* spores (0.6 g) were kept in hermetic glass vials of 125 mL (Ball®, Jarden Corp., Muncie, Ind., USA) sealed with metal caps containing rubber septa. In each glass vial were injected for 40 minutes at a rate of 40 mL.mim$^{-1}$ pure carbon dioxide, nitrogen, helium or hydrogen, as well as 100% or 21% oxygen, equilibrated with $N_2$ (Airgas East, Inc., Salem, N.H., USA). In the vials where $O_2$ was not injected, the concentration of this gas was measured following the injection to ensure that the environment did not contain non-detectable concentrations of $O_2$. Gas samples (500 μL) were collected from each vial with an hermetic syringe (model 1750, Hamilton Company, Reno, Nev., USA), and injected into a gas chromatograph (Varian Aerograph, Walnut Creek, Calif., USA) equipped with a thermal conductivity detector. The peak heights were compared to a standard commercial product containing 6.96% $O_2$ and 4.91% $CO_2$ equilibrated with $N_2$. Each treatment consisting of the gas exposure was repeated three or four times. To minimize gas exchange ($O_2$) during storage, glass vials of 125 mL were kept in larger Ball® jar hermetic containers (0.95 L) containing the same gas mixture. Using this arrangement, the glass bottles were incubated at 50° C. for 60 days. Temperatures were monitored continuously with two digital data loggers (Hobo®, Onset Computer Corp., Bourne, Mass., USA) per incubator. After this storage, the $O_2$ concentration in each vial was again determined as indicative of the system hermeticity. The water activity of the spores was measured at 25° C. with a water activity meter (LabMaster-$a_w$, Novasina, Pfaffikon, Switzerland) and determined the germination. The viability was determined directly by suspending the powder conidia in water-surfactant solution and disposing this material on yeast extract agar-benomyl medium extract (yeast extract Agar/benomyl medium—YEA). The solutions (water-surfactant) were equilibrated with ambient temperature. After running each rehydration protocol, the inoculated agar block (on glass slides) were incubated in paraffinized Petri dishes at 25° C. in the dark and germination counts were performed 24 after inoculation (p.i.). Conidia was considered as germinated when a germ tube of any size was visible at 400× magnification with phase contrast illumination. At least 200 conidia were examined in several microscopic fields for each suspension replicate of each experimental treatment.

The experiment was repeated on a different date without treatment with 21% $O_2$. The vials injected with gases except $O_2$ in which considerable gas exchange occurred (final content of $O_2$ f>3.5%) were discarded. The data were transformed into square root of the arcsine and analyzed using one-factor analysis of variance. The mean values were compared by Tukey-Kramer HSD or t-test and considered statistically different at a significance level of 5%. Data were analyzed using the JMP statistical software package (SAS Institute Inc., Cary, N.C., USA).

FIG. 1 shows that the final water activity for the spores in the first assay did not change with gas treatment (P=0.4150, $F_{5,13}$=1,1); the global average water activity was 0.099±0.0248. Significant differences in germination were observed after 60 days at 50° C. (P<0.0001, $F_{5,13}$=122.0) and while exposure to $N_2$, $CO_2$, $H_2$ and He produced viabilities equivalents in the range of 40-51%, germination rates were very low or even the absence of viable spores were recorded at 21% and 100% $O_2$, respectively.

As in the first experiment, the treatments did not produce significant differences in final water activity of the spores (P=0.29, $F_{=3,11}$=1,4), average water activity of 0.119±0.0021 between treatments. Injection of 100% $O_2$ resulted again in no survivors (21% $O_2$ was not tested). The storage of all other gases resulted in superior viability to treatment with $O_2$ but low, equivalent (range 10-13%) (FIG. 1B). These germination rates were markedly lower than the range of 49-51% observed in the first test, due to the lower water activity of the spores in the first experiment. Except for vials injected with $O_2$, residual $O_2$ concentrations (1.6%-1.9%) did not differ between the vials injected with gases (P=0.73, $F_{2,8}$=0.3).

Example 2

$N_2$ and $CO_2$ Injection for Storage of Spores at Different Temperatures

Using the same arrangement described in the previous item, samples of spores were injected with 20% $CO_2$ and 80% $N_2$. Four samples were tested for each treatment regarding the residual $O_2$ and final water activity after storage for 45, 91, 180 and 240 days at 40° C. The experiment was repeated on a different date. Additionally, experiments were performed to investigate the effects of storage at 25° C. (evaluations after 46, 120, 180, 365 and 400 days storage) and 50° C. (evaluations after 15, 30, 47, 75 and 90 days storage). In all cases, viability was also determined in the "day zero", that is, immediately before storing in incubators at different temperatures. Different bottles were sampled on a single date of evaluation and therefore, this study did not use repeated measures design.

The data were transformed into square root of the arcsine and analyzed using one-factor analysis of variance. The mean values were compared by Tukey-Kramer HSD or t-test and considered statistically different at a significance level of 5%. Data were analyzed using the JMP statistical software package (SAS Institute Inc., Cary, N.C., USA).

Figure 2:
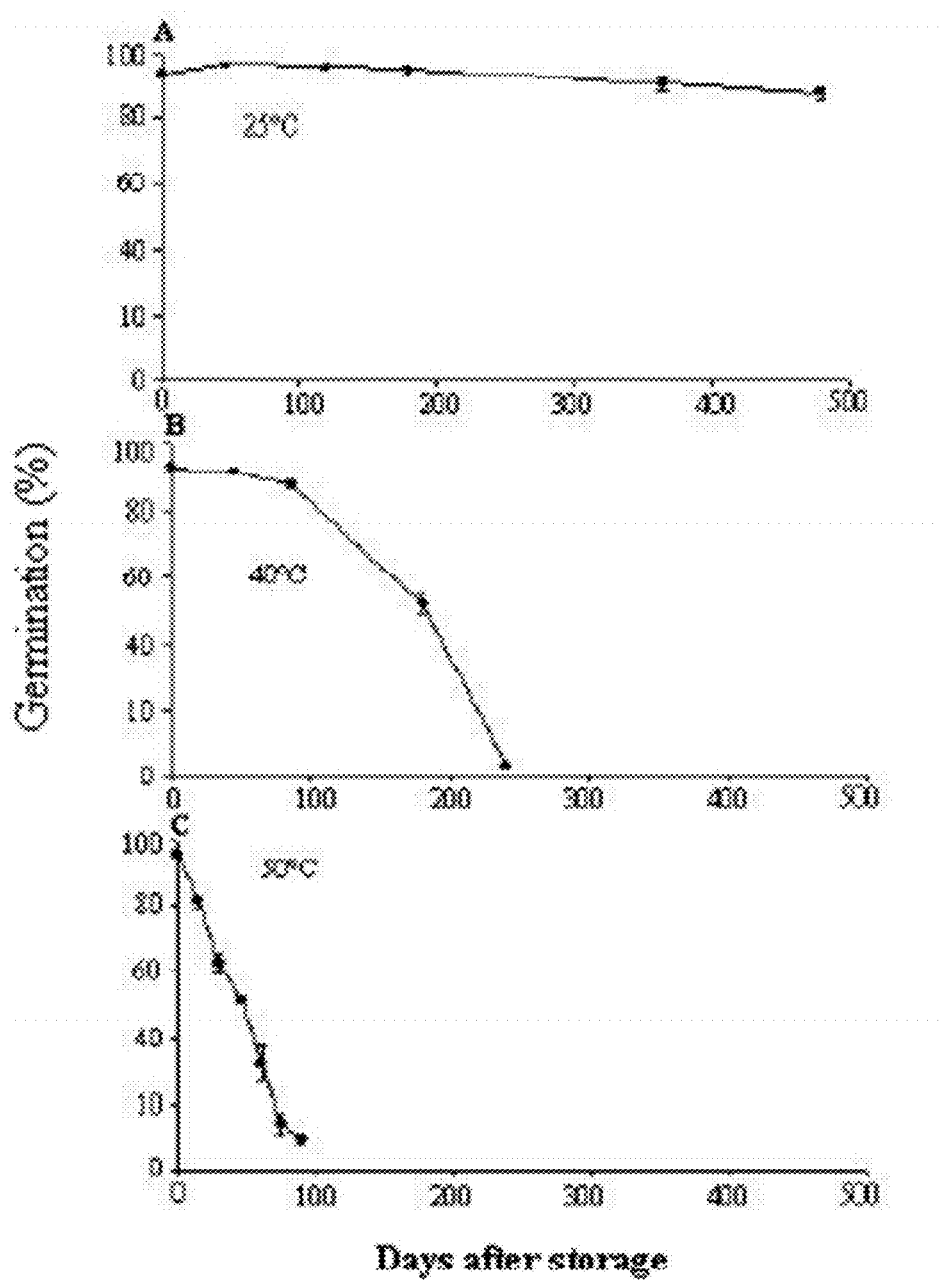
FIG. 2: Viability of conidia of *Beauveria bassiana* after injection of 20% $CO_2$ (+80% $N_2$) and storage at 25, 40, or 50° C.

In the storage experiment at 25° C. it was observed a significant decrease in viability (P=0.0002, $F_{5,18}$=8.8) but the decrease was gradual and small, and the viability was higher than 90% at 365 days and 87% at 480 days post-storage, as seen in FIG. 2. The water activity of the spores increased from 0.104 at 46 days after storage to 0.204 at the end of the experiment (P<0.0001, $F_{[4,15]}=36.3$) and the mean concentration of residual $O_2$ increased from 0.5% to 12.4% (P<0.0001, $F_{4,15}=38.0$).

In the experiment at 40° C., there was a statistically significant loss of viability during the first 3 months of storage, but the decrease was only 6 percentage points (from 93 to 87%). This was followed by a rapid decline to 4% viability at 240 days after storage (ANOVA P<0.0001, $F_{4,34}=361.7$). During the interval between 45 and 240 days, the average concentration of residual $O_2$ increased from 1.2% to 6.6% (P=0.0002, $F_{3,28}=9.4$) and water activity increased from 0.104 to 0.145 (P<0.0001, $F_{3,27}=35.4$).

At 50° C. the initial viability decreased rapidly from 96 to 81% in the first 15 days, and approximately 10% at 90 days after storage (P<0.0001, $F_{6,21}=129.1$). The residual $O_2$ increased from 0.8% at 15 days to 3.2% at 90 days post-storage (P=0.0074, $F_{5,18}=4.5$), while the water activity of the spores did not change significantly during this period (from 0.104 at 15 days to 0.098 and 90 days: P=0.3448, $F_{5,18}=1.2$).

Example 3

Gas Injection and Employment of Active Packaging (AP)

Beauveria bassiana spores were dehydrated with NaOH in glass vials of 125 mL for 1 day at 25° C., resulting in 0.083±0.001 water activity. Several random samples were transferred to glass vials and injected with $N_2$. The loss of $O_2$ was reduced using a dual filling system with glass containers. The remaining samples (0.6 g) were subjected to one of the three AP treatments comprising: i) aluminum bags (8×8.5 cm) with a $O_2$ and moisture RP-3A absorber sachet; ii) a $O_2$ absorber film (code M-0034, lot 19208A, 88.9× 63.5×0.3 mm CSP Technologies, Auburn, Ala., USA) plus a humidity absorber film (CSP Technologies, code M-0026, lot 02208A, 63.5×38.1×0.6 mm) or; ii) a film having dual action as $O_2$ and humidity absorber (CSP Technologies, code M-0033, lot 10808A, 76.2×76.2×0.6 mm). For control, spores were maintained in 30 mm thick polyethylene bags (code P827-2.1.2; Empac Agroindustrial Ltda Plastics, Brasilia, Brazil) with a RP-3A sachet.

After preparation, all packages with spores were pre-incubated at 25° C. for 5 days and then transferred to 50° C. The residual $O_2$ of the glass vials injected with $N_2$ was checked immediately before incubation at elevated temperature. For all treatments, three containers were used for destructive determination of water activity and viability of the spores immediately prior to transfer to 50° C. Spores were incubated at 50° C. for 56 or 120 days. After storage, water activity was measured and conidial viability was assessed. For each treatment and date, four packages independently prepared were destructively evaluated and, therefore, repeated measures design was not adopted.

Example 4

Sachets for Modified Atmosphere Samples of Beauveria bassiana spores were stored in glass vials of 125 mL with calcium sulfate desiccant (Drierite™ 8-mesh indicator, W. A. Hammond Drierite Co., Xenia, Ohio, USA) for two days at 25° C. The water activity of the spores before filling was 0.019±0.0005. In another treatment the spores were maintained on saturated NaCl solution for 2 days at 25° C., which resulted in water activity of 0.738±0.0007 before filling. The samples were then transferred to laminate bags (10×12 cm) containing one of the following sachets for atmosphere modification: $O_2$ and humidity absorber RP-SA, $O_2$ absorber Ageless® ZPT 1000 (Mitsubishi Gas Chemical Co., Japan), $O_2$ and $CO_2$ absorber OxyFree™ 504A (Tianhua Tech, China), $O_2$ absorber and $CO_2$ generator OxyFree™ generator 504E (Tianhua Tech, China), or humidity absorber based on Drierite™ (56.7 g). As control, laminated bags without sachet were used. The bags were incubated at 50° C. without the pre-incubation period, quantifying the water activity of the spores and the germination counting after 45 days. Each treatment (type of sachet vs. Initial water activity) was repeated four times.

TABLE 1

Germination (%) of Beauveria bassiana spores determined after storage for 45 days at 50° C. in bags containing absorber sachets and/or gas and water vapour generators.

| Sachet | Low initial $a_w$ (0.019) | | High initial $a_w$ (0.738) | |
| --- | --- | --- | --- | --- |
| | Final $a_w$ | % | Final $a_w$ | % |
| Ageless ($O_2$ absorber) | 0.807 ± 0.0012 a | 0.0% c | 0.819 ±: 0.0015 a | 0.0% c |
| Drierite ™ (humidity absorber) | 0.022 ± 0.0003 e | 5.2 ± 0.7% b | 0.23 ± 0.0007 e | 7.3% ± 1.3% b |
| RP-3A ($O_2$/humidity absorber) | 0.794 ± 0.0003 c | 79.0 ± 1.3% a | 0.022 ± 0.0003 e | 72.8% ± 3.2% a |
| 504 A ($O_2$ and $CO_2$ absorber) | 0.704 ± 0.0003 c | 0.0% c | 0.729 ± 0.0009 c | 0.0% c |
| 504 E ($O_2$ absorber and $CO_2$ generator) | 0.761 ± 0.0035 b | 0.0% c | 0.798 ± 0.0024 b | 0.0% c |
| Without sachet (control) | 0.027 ±: 0.0003 d | 3.8 ± 0.4% b | 0.709 ± 0.0012 d | 0.0% c |

[1]In each column, means (±SE) followed by the same letter are not statistically different (Tukey HSD, α = 0.05). Germination determined through fast rehydration protocol.

The use of several modified atmosphere sachets resulted in highly significant differences in viability of spores for both low (P<0.0001, $F_{[5,12]}=1631.4$) and the high initial water activity (P<0.0001, $F_{[5,12]}=522.4$) (Table 1). As expected, considering the absorption capacities of different sachets, final water activity of the spores in the treatments with low or high initial water activity were also markedly different. The use of sachets that release humidity during storage (Ageless, 504A and 504E) or absorb humidity but not $O_2$ (Drierite™) resulted in lower viability when compared with the use of dual action absorber, absorbing $O_2$ and humidity (RP-3A)

Example 5

Combination of Modified Atmosphere Sachets for Extension of Shelf Life

Samples of *Beauveria bassiana* spores were dried with Drierite™ for 2 days at 25° C. (resulting in water activity of 0.020±0.0008) and then transferred to 16×20 cm laminated bags with different sachets: RP-5A to absorb $O_2$ and humidity (same composition as RP-3A but suitable for larger packages) 504E to absorb $O_2$ and generate $CO_2$ or a sachet 504E plus a Drierite™ sachet (56.7 g). Each treatment was repeated three times and the water activity of the spores was determined, as well as the germination after 148 and 180 days after storage at 40° C.

The sachet which absorbs $O_2$, but releases humidity (504E) was effective when tested in conjunction with a desiccant (Drierite™), but the isolated use of sachet 504E resulted in complete loss of viability (Table 2). The strategy of combining the use of sachets was as good as the use of dual action sachet (RP-5A), both after 148 days (P<0.0001, $F_{2,6}=309.0$) and after 178 days after storage at 40° C. (P<0.0001, $F_{2,6}=2.035$).

TABLE 2

Effect of an $O_2$ absorber and $CO_2$ generator, with or without desiccant sachet on the water activity and viability of *Beauveria bassiana* spores stored at 40° C. for 5 to 6 months.

| Sachet | Day 148 Final $a_w^1$ | % | Day 178 Final $aw^1$ | % |
|---|---|---|---|---|
| 504 E ($O_2$ absorber and $CO_2$ generator) | 0.793 ± 0.0038 a | 0.0% b | 0.809 ± 0.0168 a | 0.0% b |
| 504E + Drierite ™ (humidity absorber) | 0.030 ± 0.0003 b | 81.0 ± 4.5% a | 0.030 ± 0.0003 b | 79.3 ± 1.9% a |
| RP-5A ($O_2$/humidity absorber) | 0.026 ± 0.0000 b | 83.5 ± 2.2% a | 0.028 ± 0.0003 b | 81.8 ± 0.4% a |

[1] $A_w$ initial was 0.020 ± 0.0008, and spores were not pre-incubated at moderate temperature prior to exposure to 40° C.
[2] In each column, mean (±EP) followed by the same letter are not statistically different (Tukey HSD, α = 0.05). Germination determined through fast rehydration protocol.

Example 6

Effect of Equilibrium Period on the Shelf Life

The pure spores of *Beauveria bassiana* had their water activity equilibrated inside the package prior to being exposed to high temperature regimens. The samples of *Beauveria bassiana* were kept in Drierite™ or NaCl for 2 days at 25° C., resulting in water activity of 0.020±0.0008 and 0.740±0.0018, respectively. Then, the spores were transferred to laminated bags each containing a sachet RP-3A ($O_2$ and humidity absorber) and pre-incubated for an additional period of 5 days at 25° C. before being stored at target temperatures (25, 40 and 50° C.). Alternatively, samples were kept in Drierite™ or NaCl for 7 days at 25° C., transferred to laminated bags containing RP-3A sachets and immediately stored at target temperatures without the equilibration period of 5 days at 25° C. Each treatment was repeated four times and measurements of the water activity and viability were performed after 60 days at 50° C. and 180 days at 25 or 40° C.

The final water activity of the spores did not vary between treatments at each storage temperature (Table 3). Germination percentages after 180 days at 25° C. were high (91-94%) for all treatments, except for treatment with high initial water activity and the equilibration period, in which the viability was reduced to 68%. After 180 days at 40° C., viability was 87-89% for most treatments but was significantly lower (75%) in the treatment with high initial water activity and without the equilibration period (P 0.0068, $F_{3,8}=8.7$). Finally, after 60 days at 50° C., the same tendency was observed with viabilities for almost all treatments in the range of 83-86%, except for the treatment of high initial water activity and without the equilibrium period, in which the viability was significantly reduced to 60% (P<0.0001, $F_{3,8}=37.8$).

The shelf-lives observed in this study are considerably higher than those previously obtained. Atmospheres modified after the injection of gases other than $O_2$ ($CO_2$, $N_2$, $H_2$ and He) resulted in comparable viabilities after 2 months of storage at 50° C. When testing an atmosphere of 20% $CO_2$ (+80% $N_2$) in vials, the time for spore viability dropped to 80% were superior to 91 and 15 days at a temperature of 40 to 50° C., respectively. These times are similar for the estimates obtained from the data published by Hong et al. (2001) (Hong, T D, et al. The effect of storage environment on the longevity of conidia of *Beauveria bassiana*. Mycological Research v. 105, p. 597-602, 2001), suggesting that the spores dehydrate in up to 5% humidity and stored with atmospheric air in hermetically sealed containers retained 80% viability for 80 and 17 days at 40 to 50° C., respectively. These were, until then, the longest shelf-lives ever recorded for this species of fungus in high temperatures. However, when using the active packaging (with sachets which absorb $O_2$ and humidity in hermetic packages) and an equilibration period was introduced, the viability reached unprecedented values ranging from 80 to 90% after 6 months at 40° C., or 2 months at 50° C.

TABLE 3

Effect of initial water activity and equilibration period (pre-incubation) on the germination of spores of *Beauveria bassiana* stored in laminate bags containing humidity and $O_2$ absorber sachet.

| Conditions | 180 days at 25° C. Final $a_w^2$ | % | 180 days at 40° C. Final $a_w^2$ | % | 60 days at 50° C. Final $a_w^2$ | % |
|---|---|---|---|---|---|---|
| Low initial $a_w$/pre-incubation | 0.029 ± 0.0000 a | 93.2 ± 0.4% ab | 0.028 ± 0.0003 a | 87.8 ± 0.9% a | 0.022 ± 0.0000 | 84.8 ± 3.5% a |

TABLE 3-continued

Effect of initial water activity and equilibration period (pre-incubation) on the germination of spores of *Beauveria bassiana* stored in laminate bags containing humidity and $O_2$ absorber sachet.

| Conditions | 180 days at 25° C. Final $a_w^2$ | % | 180 days at 40° C. Final $a_w^2$ | % | 60 days at 50° C. Final $a_w^2$ | % |
|---|---|---|---|---|---|---|
| Low initial $a_w$/without pre-incubation | 0.029 ± 0.0003 a | 94.0 ± 1.1% a | 0.028 ± 0.0003 a | 88.8 ± 0.8% a | 0.022 ± 0.0000 | 86.3 ± 3.8% a |
| High initial $a_w$/pre-incubation | 0.029 ± 0.0000 a | 91.0 ± 1.3% ab | 0.028 ± 0.0000 a | 88.0 ± 2.6% a | 0.021 ± 0.0000 | 82.5 ± 1.0% a |
| High initial $a_w$/without pre-incubation | 0.029 ± 0.0003 a | 88.3 ± 0.4% b | 0.028 ± 0.0003 a | 75.3 ± 2.2% b | 0.021 ± 0.0000 | 60.0 ± 3.0% b |

[1] In each column, means (± EP) followed by the same letter are not statistically different (Tukey HSD, $\alpha = 0.05$). Germination determined through fast rehydration protocol.
[2] Low and high initial $a_w$ were 0.020 ± 0.0008 and 0.740 ± 0.0018, respectively.

Example 7

Effect of the Dehydration Step (Before Packaging) on the Shelf Life

It can be verified from Table 4 that the equilibration period of 7 days at 25° C. was adopted for all treatments. However, in one experiment, it was found that the mere use of the sachet RP-3A (which absorbs water vapour and oxygen inside the package) is not sufficient to ensure high levels of germination. In the treatment "Hydration+RP-3A" the step of pre-drying the sample before packaging was not adopted and, even with the reduction of water activity to 0.050 at the end of equilibration period (and of 0.020 at the end of 16 months of storage), the final result was lower than in the previous treatment, where the water activity at the end of the equilibration period and throughout the storage period at 40° C. remained below 0.1, and within the ideal range of 0.02 to 0.03. In experiment 2, the two treatments followed the recommended steps (pre-drying, adoption of sachet(s) for absorption of humidity and oxygen, observing the equilibrium period for removal of oxygen and reduction of water activity to levels close to 0.03 before exposure to high temperatures) and thus the results were satisfactory. In the first experiment of treatment 2 a dual function sachet was used (absorbing humidity and oxygen), while in the second a sachet for each function was adopted. It is important to highlight that the processes and methods known in the art were never able to provide viability (germination percentage) of the fungus *Beauveria bassiana* in the order of 70% after 16 months of storage of conidia at 40° C.

TABLE 4

Effect of water activity ($a_w$) on the viability of *Beauveria bassiana* conidia stored at 40° C. for 18 months.

| Treatment | Day 0[b] Initial $a_w$ | Percentage of germination | 16 months Final $a_w$ | Percentage of germination |
|---|---|---|---|---|
| Experiment 1 | | | | |
| Prior dehydration + RP-3A | 0.026 ± 0.000 | 92.5 ± 1.76 a | 0.020 ± 0.000 | 71.0 ± 1.51 a |
| ($O_2/H_2O$ absorber)[a] Prior hydration + RP-3A Experiment 2 | 0.050 ± 0.001 | 89.3 ± 1.59 a | 0.020 ± 0.000 | 52.7 ± 5.02 b |
| Prior dehydration + RP-3A[a] | 0.025 ± 0.000 | 95.5 ± 1.09 a | 0.020 ± 0.000 | 71.4 ± 0.92 a |
| | 0.032 ± 0.001 | 95.2 ± 0.14 a | 0.024 ± 0.000 | 70.6 ± 1.16 a |

[a] Treatments with steps recommend in the present invention. In Treatment "Hydration + RP-3A", the failure to observe the first step (dehydration of the water activity of the spores before packaging to levels below 0.3) resulted in water activity at the end of the equilibration period higher than the optimal limit (0.02 to 0.03), leading to percentages of germination lower than in the previous treatment, where all steps recommended in the patent were observed.
[b] Data collected immediately before storage at high temperature following initial equilibration period of 7 days at 25° C.

Example 8

Effect of Active Packaging in the Shelf Life of fungus *Metarhizium anisopliae* at 40° C.

In experiments where the equilibration period (8 days at 25° C.) was observed for spores of *Metarhizium anisopliae* (Table 5), the use of sachet RP-3K (oxygen absorber but releases water vapour) was not sufficient to provide satisfactory results. Used alone, the release of water vapour increases the water activity of the spores to very high values and, consequently, the shelf-life is dramatically reduced. On the other hand, treatment with sachet RP-3A, which in addition to absorbing oxygen also absorbs water vapour inside the package, maintained the water activity of the spores within optimal values, thus contributing to elevated percentages of germination after 2 weeks storage at 40° C.

The data in Table 6 demonstrate that the method of the present invention allows the achievement of a viability (percentage of germination) in the order of 70% for the funfus *Metarhizium anisopliae* after more than 5 months storage at 40° C., which had never been possible for this species by conventional known methods. In general, the minimum acceptable viability for commercial products (mycopesticides) is in the order of 80%. Based on extrapolation of the data obtained above, this percentage would have been reached through the method of the present invention after 4 months of storage at 40° C. These values are significantly higher than that reported for example in U.S. Pat. No. 5,989,893 by Jin et al. (1999), in which the viability of approximately 80% was observed after 2 months of storage at 37° C.

TABLE 5

Effect of water activity ($a_w$) at the end of the equilibration period in the viability of spores of *Metarhizium anisopliae* stored at 40° C. for 2 weeks.

| | Day 0[b] | | | |
|---|---|---|---|---|
| Treatment | Initial $a_w$ | Percentage of germination | Treatment | 2 weeks Initial $a_w$ |
| Desiccation + RP-3A ($O_2/H_2O$ absorber)[a] | 0.028 ± 0.001 | 80.0 ± 4.00 a | 0.027 ± 0.001 | 78.9 ± 2.21 a |
| Desiccation + RP-3K ($O_2$ absorber) | 0.246 ± 0.005 | 79.3 ± 5.13 a | 0.286 ± 0.006 | 26.9 ± 10.45 b |

[a]Treatments with steps recommend in the present invention.
[b]Data collected immediately before storage at high temperature following initial equilibration period of 8 days at 25° C.

TABLE 6

Percentage of germination of spores after storage of *Metarhizium anisopliae* at 40° C. for 5.4 months.

| | Day 0[b] | | | |
|---|---|---|---|---|
| Treatment | Initial $a_w$ | Percentage of germination | Treatment | 16 months Initial $a_w$ |
| RP-3A ($O_2/H_2O$ absorber)[a] | 0.037 ± 0.001 | 94.5 ± 1.73 | 0.021 ± 0.001 | 68.3 ± 3.32 |

[a]Treatments with steps recommend in the present invention.
[b]Data collected immediately before storage at high temperature following initial equilibration period of 5 days at 25° C.

It was observed in studies of the prior art reported herein that atmospheres in which air was replaced by $CO_2$ and $N_2$ increased longevity of *Beauveria bassiana* spores. Previous attempts to extend the shelf-life of this species were conducted in the presence of air, although the beneficial effects of removal of $O_2$ (or increasing $CO_2$ concentration) during the short term shelf-life of *Metarhizium anisopliae* have been demonstrated for decades by Clerk and Madelin (19A5) (Clerk, C G; Madelin, M. F. The longevity of conidia of three insect-parasitizing hyphomycetes. Transactions of the British Mycological Society 48, 193-209, 1965). U.S. Pat. No. 5,989,898 discloses that spores of *Metarhizium* dehydrated with Drierite™ and stored at atmospheres supposedly without $O_2$ obtained with the use of Ageless sachet inserted in bags impermeable to humidity and gas showed 74% viability after 2 months at 37° C., and showed no viability if maintained in bags without $O_2$ absorber or with high relative humidity ranging from 40 to 100%. Leite et al. (2002) (Leite, L. G., et al. Preservação de micélio de *Batkoa* sp. e *Furia* sp. (Entomophthorales) em combinação com dessecantes e redutores de oxigênio [Preservation of mycelium of *Batkoa* sp. and *Furia* sp. (Entomophthorales) in combination with desiccant and oxygen reducers]. Arquivos do Instituto Biológico 69, 117-122, 2002) Preserved dry mycelia of *Batkoa* sp. and *Furia* sp. for 3 months at 23° C. using Ageless and silica gel, but further studies regarding entomopathogenic fungi packages in modified atmosphere are not known.

In non-hermetic packages the availability of air to the spores is significant (Hong, T. O., et al. Saturated salt solutions for humidity control and the survival of dry powder formulations and or of *Beauveria bassiana* conidia. Journal of Invertebrate Pathology. v. 89, p. 136-143, 2005) and therefore the results observed for longevity of spores are discouraging. The present invention showed that the adoption of plastic polymers with high permeability to $O_2$ and humidity are totally undesirable for mycopesticides packaging, even if combined with an efficient sachet for active packaging. Gas injection (for 40 min) in glass containers proved far more efficient than the use of non-hermetic packaging, but less efficient than the use of laminates (+sachets of active packaging) for extending the life-shelf of *Beauveria bassiana* spores in the present technology due to the presence of water activity greater than desired after the injection of gas, air exchanges with the external environment and due to the inability of the gas injection protocols used to enable greater removal of $O_2$ present in the packaging. The study Teshler et al (2007) (Teshler, M. P. et al. Increased shelf life of the bioherbicide through combining modified atmosphere packaging and low temperatures. Biocontrol Science and Technology 17, 387-400, 2007). disclosed that the residual $O_2$ concentration was 0.26% after gas injection in laminated packaging. Water activity remained at low and constant levels after hermetically filled with aluminum and the use of an efficient $O_2$ and humidity absorber. In anhydrobiotic organisms, isolated enzymatic reactions may occur which lead to the production of free radicals and non-enzymatic reactions mediated by these free radicals. For example, reactions of degradation of phospholipids may occur, with accumulation of byproducts (fatty acids) in the membranes (McKersie, B. D. et al. Senaratna, T., Walker, M. A., Kendall, E. J., Hetherington, P. R. Deterioration of membranes during aging in plants: Evidence for free radical mediation. In: L. D. Nooden, L. D., Leopold, A. C. (Eds.), Senescence and Aging in Plants. San Diego: Academic Press, p. 442-464, 1088). However, the aging under atmospheric conditions and free from $O_2$ and extremely dry is considerably slower than under non-hermetic conditions.

Most active packaging sachets used in the food industry tested was not effective to extend the viability of *Beauveria bassiana* spores, whether because the water activity levels of spores increased to undesirable levels or because $O_2$ was not reduced to low levels. A sachet with dual action, able to absorb O2 and humidity, was more efficient than sachets that have only a single attribute. Although the $CO_2$ is known to have fungistatic activity on some fungi in growth (Tabak and Cooke, 1968; Abellana et al. 2000), no deleterious effect was observed on stored entomopathogenic spores, which suggests the possibility of using active packaging by using $O_2$ absorber and $CO_2$ emitter sachets.

The shelf-life of approximately one year was recorded for the relatively thermotolerant *M. acridum* with humidity of 6.2% (but the same was not achieved for spores with 7.0% water content) at 27-32° C. and stored under vacuum (Hong et al, 1999), as well as oil formulations of *Beauveria bassiana* at 25° C. (Wraight et al, 2001) The present invention achieved shelf-life of 8 months for spores with 2.1 to 2.4% humidity packaged in active packaging, which is sufficient time for distributions in regions with average temperatures near 40° C. Experiments were also conducted at 50° C. Similar or higher temperatures can be achieved in certain regions (Hong, T. D., Ellis, R. H., Moore, D. Development of a model to predict the effect of temperature and moisture on fungal spore longevity. Annals of Botany, v. 79, p. 121-128, 1997) or during transportation (Ostrem and Godshall, 1979).

In addition to factors intrinsically related to storage, pre-storage factors such as the original quality of fungal propagules, which in turn is influenced by the culture conditions (Agosin, E. et al. Effect of culture conditions on spore shelf life of the biocontrol agent Trichoderma harzianum. World Journal of Microbioiogy and Biotechnology v. 13, p. 225-232, 1997; Frey, S., Magan, N. Production of the fungal biocontrol agent Ulocladium atrum by submerged fermentation: accumulation of endogenous reserves and shelf-life studies. Applied Microbiology and Biotechnology, v. 56, p. 372-377, 2001; Tarocco et al. Optimization of erythritol and glycerol accumulation in conidia of Beauveria bassiana by solid-state fermentation, using response surface methodology. Applied Microbiology and Biotechnology v. 68, p. 481-488, 2005), drying and collecting processes (Sandoval-Coronado, C. F. et al. Drying and formulation of blastospores of Paecilomyces fumosoroseus (Hyphomycetes) produced in two different liquid media. World Journal of Microbiology and Biotechnology v. 17, p. 423-428, 2001; Bateman, R. Constraints and enabling technologies for mycopesticide development. Outlooks on Pest Management April, p. 64-69. 2004; Jackson, M. A., Payne A. R., Evaluation of the desiccation tolerance of blastospores of Paecilomyces fumosoroseus (Deuteromycotina: Hyphomycetes) using a labscale, air-drying chamber with controlled relative humidity. Biocontrol Science and Technology, v. 17, p. 709-719, 2007.) and formulation (Sandoval Coronado. C. F. Luna-Olvera, H. A., Arevalo-Nino, K, Jackson, M. A., Poprawski, T. J., Galan-Wong, L. J., Drying and formulation of blastospores of Paecilomyces fumosoroseus (Hyphomycetes) produced in two different liquid media. World Journal of Microbiology and Biotechnology v, 17, p. 423-428, 2001: Batta, Y. A. Production and testing of novel formulations of the entomopathogenic fungus Metarhizium anisopliae (Metschinkoff) Sorokin (Deuteromycotina:Hyphomycetes). Crop Protection, v. 22, p. 415-422, 2003; Friesen, T. J. et al. Effect of conditions and protectants on the survival of Penicillium bilaiae during storage. Biocontrol Science and Technology, v. 16, p. 80-08, 2006) have profound impact on longevity. This invention shows that it is necessary to dry the spores packaged and subjected to mild conditions before exposure to high temperatures so that high initial water activity reaches the desired levels, and thus avoid premature death or debilitation of the spores. Post-storage factors such as the germination protocol, although not directly related to shelf life, can result in erroneous viability if not performed properly. The shelf lives shown in this example were estimated with an emphasis on a rapid rehydration protocol (without prior exposure of the spores to a regime of slow rehydration inside a humid chamber for 24 h).

The water activity of pre-dehydrated spores maintained in hermetic bags with Drierite™ or $O_2$ and humidity absorber were consistently in the range of 0.010 to 0.030 (equilibrium relative humidity of 1.9-3.0%). This small variation was observed between the readings taken in winter (laboratory air cooler and drier) and seasons with higher temperature and relative humidity. The importance of dehydrating the airborne fungal spores to extend the shelf-life has been shown previously (Clerk, C. G.; Madelin, M. F. The longevity of conidia of three insect parasitizing hyphomycetes. Transactions of the British Mycological Society 48, 193-209, 1965; Feng, M. G., Poprawski, T. J., Khachatourians, G. G. Production, formulation and application of the entomopathogenic fungus Beauveria bassiana for insect control: current status. Biocontrol Science and Technology v. 4, p 3-34, 1994; Shimizu, S; Mitani, T. Effects of temperature on viability of conidia from Beauveria bassiana in oil formulations. Japanese Journal of Applied Entomology and Zoology v. 44, p. 51-53, 2000). In studies with hermetic storage in which air was not removed from the packages (Hong, T. D., et al Gunn, J The effect of storage environment on the longevity of conidia of Beauveria bassiana. Mycological Research 105, 597-602, 2001) reported that the longevity of two isolates of Beauveria bassiana did not increase significantly when the humidity content in storage decreased to values below the range of 4.6 to 5.2%, in equilibrium with relative humidities of 11-14% at 20° C. In this study, the best water activity of the spores was consistently associated with Driorite™, which has moisture content considerably lower than 5%. The results obtained in the present invention suggest that under practically anaerobic conditions (<0.03% $O_2$) optimal water activities for storage are lower than under aerobic atmospheres.

The invention claimed is:

1. Method for packaging fungal spores, characterized by comprising the steps of:
   (i) reducing initial water activity of the spores to below 0.3;
   (ii) placing the spores into a gas- and water-vapour impermeable packaging containing one oxygen absorber agent and one humidity absorber agent;
   (iii) keeping the spores in the packaging for at least two days at temperatures between 15 and 25° C.

2. The method according to claim 1, characterized in that said humidity absorber agent is selected from calcium sulfate or silica gel.

3. The method according to claim 1, characterized in that said agents are in the form of one or more sachets which are nontoxic to the spores.

4. The method according to claim 1 characterized by the fact that said gas- and water-vapour-impermeable packaging is selected from the group consisting of glass, laminate materials containing aluminum, and ceramic.

5. The method according to claim 1 characterized by the fact that the final water activity values, after step (ii) are lower than 0.1.

6. The method according to claim 1, characterized by the fact that said spores are selected from the group of genera Metarhizium, Beauvoria, Isaria, Lecanicillium, Nomuraea and Trichoderma.

7. The method according to claim 1 characterized by the fact that the final water activity values, after step (ii) are between 0.02 and 0.03.

8. The method according to claim 1, characterized in that said spores are kept in the packaging for at least five days at temperatures between 15 and 25° C.

9. The method according to claim 1, characterized in that said spores are kept in the packaging for at least eight days at temperatures between 15 and 25° C.

* * * * *